United States Patent
Al-Shafei et al.

(10) Patent No.: US 11,090,643 B2
(45) Date of Patent: Aug. 17, 2021

(54) SYSTEMS AND METHODS FOR ZEOLITE CATALYST PORE BLOCKING MODIFICATIONS FOR HYDROCARBON CONVERSION REACTIONS

(71) Applicants: Saudi Arabian Oil Company, Dhahran (SA); King Fahd University of Petroleum and Minerals, Dhahran (SA)

(72) Inventors: Emad Naji Al-Shafei, Dhahran (SA); Oki Muraza, Dhahran (SA); Ki-Hyouk Choi, Dhahran (SA); Ali Al-Nasir, Dhahran (SA); Zain Hassan Yamani, Dhahran (SA); Idris Akolade Bakare, Dhahran (SA); Mohammad Al-Abdullah, Dhahran (SA)

(73) Assignees: SAUDI ARABIAN OIL COMPANY, Dhahran (SA); KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/675,735

(22) Filed: Nov. 6, 2019

(65) Prior Publication Data
US 2021/0129127 A1    May 6, 2021

(51) Int. Cl.
*C01B 39/02* (2006.01)
*B01J 37/02* (2006.01)
(Continued)

(52) U.S. Cl.
CPC .......... *B01J 37/0018* (2013.01); *B01J 29/40* (2013.01); *B01J 29/90* (2013.01); *B01J 37/04* (2013.01);
(Continued)

(58) Field of Classification Search
CPC ........ C01B 39/026; C01B 39/38; B01J 29/40; B01J 29/90; B01J 37/0018;
(Continued)

(56) References Cited

U.S. PATENT DOCUMENTS 4,336,234 A   6/1982   Leutner et al.
4,376,036 A   3/1983   Garwood et al.
(Continued)

FOREIGN PATENT DOCUMENTS

EP          0863109 A1     9/1998
WO       2010011958 A2     1/2010
(Continued)

OTHER PUBLICATIONS

Rosas et al, "Catalytic Dehydration of Glycerine to Acrolein" Glycerine Production and Transformation—An Innovative Platform for Sustainable Biorefinery and Energy Nov. 8, 2018 (Year: 2018).*
(Continued)

*Primary Examiner* — David M Brunsman
(74) *Attorney, Agent, or Firm* — Bracewell LLP; Constance G. Rhebergen; Kevin R. Tamm (57) ABSTRACT

Systems and methods for production of externally-pore-blocked, internally-pore-opened modified zeolite crystals, the method including mixing zeolite crystals with an organic pore blocking agent; heating the zeolite crystals mixed with the organic pore blocking agent to block internal pores of the zeolite crystals and produce internally-pore-blocked zeolite crystals; mixing the internally-pore-blocked zeolite crystals with an external pore blocking agent; and calcining the internally-pore-blocked zeolite crystals mixed with the external pore blocking agent, to re-open internal pores via decomposition of the organic pore blocking agent and to block external pores via formation of a silica layer over external pores of the zeolite crystals, forming the externally-
(Continued)

pore-blocked, internally-pore-opened modified zeolite crystals.

32 Claims, 3 Drawing Sheets (51) Int. Cl.
| | |
|---|---|
| C10G 47/16 | (2006.01) |
| B01J 37/00 | (2006.01) |
| B01J 29/40 | (2006.01) |
| B01J 29/90 | (2006.01) |
| B01J 37/04 | (2006.01) |
| B01J 37/08 | (2006.01) |
| B01J 38/12 | (2006.01) |
| C01B 39/38 | (2006.01) |
| C10G 11/05 | (2006.01) |

(52) U.S. Cl.
CPC .............. *B01J 37/08* (2013.01); *B01J 38/12* (2013.01); *C01B 39/026* (2013.01); *C01B 39/38* (2013.01); *C10G 11/05* (2013.01); *C10G 47/16* (2013.01); *B01J 2229/126* (2013.01); *B01J 2229/32* (2013.01); *B01J 2229/34* (2013.01); *C01P 2002/72* (2013.01); *C01P 2004/84* (2013.01); *C10G 2300/1081* (2013.01); *C10G 2300/1088* (2013.01); *C10G 2300/70* (2013.01); *C10G 2400/30* (2013.01)

(58) Field of Classification Search
CPC .............. B01J 2229/126; B01J 2229/32; B01J 2229/34; C10G 47/16; C01P 2004/84
See application file for complete search history.

(56) References Cited

U.S. PATENT DOCUMENTS

| | | | |
|---|---|---|---|
| 4,465,886 | A | 8/1984 | Rodewald |
| 4,950,835 | A | 8/1990 | Wang et al. |
| 5,516,736 | A | 5/1996 | Chang et al. |
| 6,645,370 | B2 | 11/2003 | Verduijn et al. |
| 6,746,659 | B2 | 6/2004 | Pinnavaia et al. |
| 6,843,977 | B2 | 1/2005 | Pinnavaia et al. |
| 6,864,200 | B2 | 3/2005 | Das et al. |
| 6,869,906 | B2 | 3/2005 | Pinnavaia et al. |
| 2007/0227351 | A1 | 10/2007 | Garcia-Martinez |
| 2012/0275993 | A1 | 10/2012 | Olson |
| 2014/0100401 | A1 | 4/2014 | Das |
| 2015/0166899 | A1 | 6/2015 | Shi et al. |

FOREIGN PATENT DOCUMENTS

| | | |
|---|---|---|
| WO | 2017005712 A1 | 1/2017 |
| WO | 2017005715 A1 | 1/2017 |

OTHER PUBLICATIONS

Rodrigues et al, "Glycerol dehydration catalyzed by MWW zeolites and the changes in the catalyst deactivation caused by porosity modification", Applied Catalysis A: General vol. 495, Apr. 5, 2015, pp. 84-91 (Year: 2015).*
Chudasama et al, "Pore-Size Engineering of Zeolite A for the Size/Shape Selective Molecular Separation", Ind. Eng. Chem. Res. 2005, 44, 6, 1780-1786 (Year: 2005).*
Guisnet et al, "Deactivation by coking of zeolite catalysts. Prevention of deactivation. Optimal conditions for regeneration", Catalysis Today vol. 36, Issue 4, Jun. 20, 1997, pp. 477-483 (Year: 1997).*
Berger, C., et al., "Hydroconversion of methylcyclohexane on TEOS-modified H-ZSM-5 zeolite catalysts: Production of a high-quality synthetic steamcracker feedstock", Science Direct, Microporous and Mesoporous Materials 59, 2003, pp. 1-12.
Ding, W., et al., "The Effects of Silanation of External Acid Sites on the Structure and Catalytic Behavior of Mo/H-ZSM5", Journal of Catalysis, 206, pp. 14-22, 2002.
Kikuchi, S., et al., "Study on Mo/HZSM-5 catalysts modified by bulky aminoalkyl-substituted silyl compounds for the selective methane-to-benzene (MTB) reaction", Journal of Catalysis, 242, 2006, pp. 349-356.
Xie, Z., et al., "An Overview of Recent Development in Composite Catalysts from Porous Materials for Various Reactions and Processes", International Journal of Molecular Sciences, 2010, 11, pp. 2152-2187.
You, Y., et al., "Liquid-phase catalytic degradation of polyethylene wax over silica-modified zeolite catalysts", Polymer Degradation and Stability, 72, 2001, pp. 329-336.
Goodarzi, et al., "Synthesis of mesoporous ZSM-5 zeolite encapsulated in an ultrathin protective shell of silicalite-1 for MTH conversion", Microporous and Mesoporous Materials, vol. 292, 2020.
Partial International Search Report for PCT Application No. PCT/US2020/058631 dated Feb. 25, 2021.
Qian, et al., "A facile route to cage-like mesoporous silica coated ZSM-5 combined with Pt immobilization", Journal of Materials Chemistry A, RSC Publishing, pp. 7525-7532, 2013.
Zhang, et al., "Increasing para-Xylene Selectivity in Making Aromatics from Methanol with a Surface-Modified Zn/P/ZSM-5 Catalyst", ACS Catalysis, vol. 5, pp. 2982-2988, 2015.

* cited by examiner

SYSTEMS AND METHODS FOR ZEOLITE CATALYST PORE BLOCKING MODIFICATIONS FOR HYDROCARBON CONVERSION REACTIONS

BACKGROUND

Field

The present disclosure relates to systems and methods for targeted pore blocking of zeolite catalysts. Specifically, the disclosure presents systems and methods to only block external pores in a zeolite catalyst while not blocking internal pores, for example in a ZSM-5 type zeolite catalyst, producing a modified zeolite for use as a catalyst in hydrocarbon cracking and related hydrocarbon conversion processes.

Description of the Related Art

Hydrocarbon conversion reactions for petrochemical processes largely utilize zeolite-type material for catalysts. Zeolites have been the subject of continuous developments and modifications for many years. The zeolites of Beta-type (BEA), Y-type, and ZSM-5-type structure are important as catalytic materials for chemical industry applications. However, the structure of ZSM-5 zeolite catalyst is known to be unstable under steam cracking conditions, and several defects occur during use, for example loss of alumina or combined loss of silica and alumina from the zeolite framework structure. This leads to reduction of zeolite catalytic activities and potential deactivation.

Zeolites are used in automotive emissions control, industrial off-gas purification, volatile organic carbon (VOC) reduction, and nitrogen oxides (NOx) reduction technologies. As process catalysts, they are used for fuel upgrading, production of petrochemical intermediates, and processing chemicals. BEA zeolites, for example, are also useful for adsorption purposes, such as odor removal and active carbon replacement. Growing demand for new catalytic chemical processing has led to a rise in the need for more reactive and selective catalysts. Nanotechnology for the production of catalytic material is essential to overcoming catalytic reaction limitations by allowing for greater dispersion of reactive catalysts, which leads to higher turnover of hydrocarbon conversion.

Under reaction conditions in a stream of steam, the framework of ZSM-5 zeolite is negatively impacted by the steam, and the acidity of the catalyst has been reported to be reduced due to several factors, such as alumina leached from the framework. Additionally, the aluminum oxidation state may be affected and changed from a reactive tetrahedral phase to an inactive octahedral phase. When used with steam, for non-modified zeolites, alumina is usually leached out from the framework of zeolites, and then the zeolite experiences loss in acidity, texture properties, reactivity, and in the shape selectivity reactions via micropores of the zeolite.

ZSM-5 zeolite catalyst can be unstable catalytically for hydrocarbon conversions and reactions, in part, due to a fast coking rate. Also, the zeolite of ZSM-5 being an unstable catalyst in the presence of steam, as noted, can result in a reduction of the surface acidity and affects the conversion and selectivity of desired reactions.

Proposed improvements for ZSM-5 zeolite as a catalyst material for reactions, in order to maintain reactivity and prevent coking, include introduction of noble metals or transition metal oxides. Carbonic deposition via methane gas at certain coking temperatures can assist in enhancing the stability and coking resistance of zeolites, such as ZSM-5 zeolite. Several technologies suggest the importance of adding phosphorous, via the addition of phosphoric acid, or the addition of silica, in order to improve zeolite catalyst reaction selectivity and stability.

In the state of the art, methods of silica coating over zeolite use silica for coating external and internal pores of zeolite with no specific or targeted location control. Existing zeolite modification systems and methods are inadequate for targeted pore blocking, for example in ZSM-5 and related catalysts.

SUMMARY

Applicant has recognized a need for systems and methods to continuously and consistently produce targeted pore blocking in zeolite catalysts, for example ZSM-5 zeolite catalysts. Prior art technical problems include catalyst deactivation when used in hydrocarbon conversion reactions with steam. In embodiments of systems and methods disclosed here, zeolite catalysts are modified to exhibit only external pore blocking in the modified zeolite structure, without or in the absence of internal pore blocking. A pore blocking organic agent is applied to block pores in a zeolite material prior to doping silica from a silica agent, and this process is followed by re-opening once again internal pores during calcining.

Embodiments of the systems and processes disclosed here improve zeolite stability under harsh steam conditions and increase pore selectivity during reactions for the hydrocarbon conversion of paraffins, iso-paraffins, in addition to or alternative to olefins, to produce aromatics for petrochemical and refinery applications. Modified zeolite catalysts produced here can be used to efficiently and continuously convert hydrocarbons such as paraffins, iso-paraffins, in addition to or alternative to olefins, to alkylbenzenes in the presence of steam.

In certain embodiments, systems and processes are designed to selectively block internal pores of zeolites by using one or more organic pore blocking agent in a first step. In a second step, a silica agent is applied in order to deposit a silica layer over external zeolite surfaces. In a third step, internal pore surfaces blocked by the organic pore blocking agent are re-opened at selected calcination temperatures. Embodiments disclosed here are applicable to zeolite materials which contain internal pores and external pores. The method is applicable to zeolites such as small-pore zeolites (8-membered rings), medium-pore zeolites (10-membered rings) and large-pore zeolites (12-membered rings). Examples include, but are not limited to, zeolite-Y or USY-type zeolites, faujasite, Beta zeolite, Mordenite zeolite, ZSM-5, ZSM-11, Ferrierite, MCM-22, X-type zeolites, SBA-15, ZSM-12, EU-1, ZSM-22, ZSM-23, ZSM-35, ZSM-39, SSZ-13, SSZ-24, SSZ-13, MCM-22, SAPO-18, SAPO-34, SAPO-37, SAPO-41, SAPO-44, Sililcalite-1, AlPO4, AlPO-11, AlPO-16, AlPO-18, Linde types zeolite of (LTA, LTL, OOF, MER), CIT-5, UTD-1, Erionite and nano-crystal zeolites.

The enhanced zeolites have resistance against coking due at least in part to external pore blocking via targeted silica layers. Disclosed frameworks enhance zeolite resistance to steam in steam streams introduced during reaction processes. After zeolite catalyst modifications, stabilized silica-coated-zeolites were tested in steam catalytic cracking fixed bed conversion processes, applying steam streams of both low and high concentration (in the range of about 10 wt. % to about 50 wt. % steam in the feed). The modified catalysts assisted in the conversion of paraffins, iso-paraffins, in addition to or alternative to olefins to produce high yields of alkylbenzenes under selected reaction conditions. Exemplified embodiments of modified ZSM-5 zeolite catalyst proved to be suitable for use as a catalyst for hydrocarbon conversions with steam and to be a stable catalyst material under steam catalytic cracking processes.

Certain embodiments of systems and methods described here enable manufacture of stabilized zeolite by using a silica agent to deposit a silica layer over external pores while maintaining open internal pores. First, systems and methods are designed to block internal pores of a zeolite by using one or more organic pore blocking agent including, but not limited to, hexadecane ($C_{16}H_{34}$), heptadecane ($C_{17}H_{36}$), octadecane ($C_{18}H_{38}$), nonadecane ($C_{19}H_{40}$), icosane ($C_{20}H_{42}$), heneicosane ($C_{21}H_{44}$), cetyltrimethylammonium bromide, behentrimonium chloride, and 1-bromohexadecane. Other similar, suitable long-chain organic hydrocarbon materials can additionally or alternatively be used.

Next, external pores are coated by a silica agent to deposit a silica layer for semi-permanent or permanent external pore blocking. Re-opening of internal pores follows and/or occurs simultaneously with blocking the external pores by means of calcining the zeolite. Certain systems and processes consist of four units and two inline centrifuge units to modify zeolite material of ZSM-5 in order to produce active zeolites and block the external pores, which allows an increase in resistance to coking and preservation of a reactive zeolite under steam streams of low and high concentrations of steam during hydrocarbon conversion reactions.

Modified zeolites of the present disclosure successfully act as catalysts in processes, such as steam catalytic cracking, with steam present at between about 10 wt. % and about 50 wt. % in a hydrocarbon flow. Certain systems and methods disclosed here include oil/gas separators and inline centrifuges for oil/water phase separation. However, inline centrifuges are not required, as any suitable demulsifier addition can be used break mixed water/hydrocarbon phases.

Externally-pore-blocked, internally-pore-opened modified zeolite catalysts of the present disclosure, including ZSM-5 zeolite catalysts, used with both lesser and greater steam concentrations allow for efficient and continuous steam catalytic cracking for on-purpose conversion of paraffins, iso-paraffins, and/or olefins to benzene, toluene, xylenes (BTX), and methyl(s), ethyl(s), and propyl(s) benzenes products.

The process is flexible and suitable for use with mixtures of compounds in a variety of hydrocarbon streams comprising paraffins, iso-paraffins, and/or olefins produced from distillation, fluidized catalytic cracking, reformer units, dealkylation units, isomerization units, or cracker units, for example. The modified catalysts are flexible to handle mixtures of paraffin, iso-paraffins and/or olefins with impurities of organic sulfur ranging from about 1 ppm to about 10,000 ppm.

Thus, disclosed here is a method for production of externally-pore-blocked, internally-pore-opened modified zeolite crystals, the method including mixing zeolite crystals with an organic pore blocking agent; heating the zeolite crystals mixed with the organic pore blocking agent to block internal pores of the zeolite crystals and produce internally-pore-blocked zeolite crystals; mixing the internally-pore-blocked zeolite crystals with an external pore blocking agent; and calcining the internally-pore-blocked zeolite crystals mixed with the external pore blocking agent, to re-open internal pores via decomposition of the organic pore blocking agent and to block external pores via formation of a silica layer over external pores of the zeolite crystals, forming the externally-pore-blocked, internally-pore-opened modified zeolite crystals. In some embodiments, the zeolite crystals comprise ZSM-5 zeolite crystals.

Still in other embodiments, the zeolite crystals comprise at least one zeolite selected from the group consisting of: zeolite-Y, USY-type zeolite, faujasite, Beta zeolite, Mordenite zeolite, ZSM-5, ZSM-11, Ferrierite, MCM-22, X-type zeolite, SBA-15, ZSM-12, EU-1, ZSM-22, ZSM-23, ZSM-35, ZSM-39, SSZ-13, SSZ-24, SSZ-13, MCM-22, SAPO-18, SAPO-34, SAPO-37, SAPO-41, SAPO-44, Sililcalite-1, AlPO4, AlPO-11, AlPO-16, AlPO-18, Linde types zeolite of LTA, LTL, OOF, or MER, CIT-5, UTD-1, and Erionite. In some embodiments, the organic pore blocking agent is mixed with the zeolite crystals at a weight between about 2 wt. % to about 15 wt. % of the weight of the zeolite crystals.

In some embodiments, the organic pore blocking agent is mixed with the zeolite crystals at a weight between about 5 wt. % to about 10 wt. % of the weight of the zeolite crystals. Still in other embodiments, the zeolite crystals are in a protonated form. In certain other embodiments, the step of mixing zeolite crystals with an organic pore blocking agent includes mixing in an aqueous solution for between about 2 and about 3 hours without heating. Still in other embodiments, the step of heating the zeolite crystals mixed with the organic pore blocking agent comprises a first step of heating the zeolite crystals mixed with the organic pore blocking agent to between about 105° C. and about 115° C. for between about 12 and about 18 hours, in order to dry the zeolite crystals from moisture.

In other embodiments, the step of heating the zeolite crystals mixed with the organic pore blocking agent comprises a second step of heating the zeolite crystals mixed with the organic pore blocking agent to between about 250° C. and about 350° C. for between about 12 and about 18 hours, in order to have internal pores of the zeolite crystals blocked by partially decomposing the organic pore blocking agent inside internal pores. In certain embodiments, the organic pore blocking agent includes at least one compound selected from the group consisting of: hexadecane ($C_{16}H_{34}$), heptadecane ($C_{17}H_{36}$), octadecane ($C_{18}H_{38}$), nonadecane ($C_{19}H_{40}$), icosane ($C_{20}H_{42}$), heneicosane ($C_{21}H_{44}$), cetyltrimethylammonium, cetyltrimethylammonium bromide, behentrimonium chloride, and 1-bromohexadecane. Still in other embodiments, the step of mixing the internally-pore-blocked zeolite crystals with an external pore blocking agent comprises mixing the external pore blocking agent comprising an orthosilicate compound and an organic solvent.

In certain embodiments, the orthosilicate compound comprises at least one compound selected from the group consisting of: tetraethyl orthosilicate, tetrabutyl orthosilicate, dichlorodimethylsilane, silicon 2-ethylhexanoate, and tetrahexyl orthosilicate. Still in other embodiments, the organic solvent comprises a compound selected from the group consisting of: methanol, ethanol, 1-propanol, 2-propanol, n-butanol, sec-butanol, and isobutanol. In certain embodiments, the step of mixing the internally-pore-blocked zeolite crystals with an external pore blocking agent proceeds for between about 1 to about 2 hours without heating. Still in other embodiments, the step of calcining the internally-pore-blocked zeolite crystals mixed with the external pore blocking agent comprises a first step of heating to between about 105° C. and about 115° C. for between about 12 to about 18 hours to dry the zeolite from any organic solvent.

In certain embodiments, the step of calcining the internally-pore-blocked zeolite crystals mixed with the external pore blocking agent comprises a second step of heating to between about 500° C. and about 750° C. for between about 12 hours and about 18 hours. Certain embodiments of the method include the step of extruding the externally-pore-blocked, internally-pore-opened modified zeolite crystals to add an alumina binder. In certain other embodiments, the externally-pore-blocked, internally-pore-opened modified zeolite crystals comprise a deposited external-pore-blocking silica layer at about 0.3 wt. % to about 5 wt. % of the total modified zeolite crystal weight. Other embodiments of the method include the step of using the externally-pore-blocked, internally-pore-opened modified zeolite crystals in steam catalytic cracking.

Additionally disclosed here is a system for carrying out the various methods disclosed, the system including an internal pore blocker unit, the internal pore blocker unit operable to heat the zeolite crystals mixed with the organic pore blocking agent; an external pore blocker unit, the external pore blocker unit fluidly coupled to the internal pore blocker unit and operable to mix the internally-pore-blocked zeolite crystals with the external pore blocking agent; and a calcining unit, the calcining unit fluidly coupled to the external pore blocker unit and operable to calcine the internally-pore-blocked zeolite crystals mixed with the external pore blocking agent.

In some embodiments, the internal pore blocker unit further comprises a mixing unit to mix zeolite crystals with the organic pore blocking agent. Other embodiments of the system include a first inline centrifuge between the mixing unit and the internal pore blocker unit and a second inline centrifuge between the external pore blocker unit and the calcining unit. Additionally disclosed is a steam catalytic cracking system to carry out hydrocarbon conversion reactions over the externally-pore-blocked, internally-pore-opened modified zeolite crystals produced by the various methods, the steam catalytic cracking system including a steam inlet; a hydrocarbon inlet; a steam catalytic cracking reactor comprising the externally-pore-blocked, internally-pore-opened modified zeolite crystals of the various methods fluidly coupled to the steam inlet and the hydrocarbon inlet; and a product separation unit fluidly coupled to the steam catalytic cracking reactor to separate products produced from hydrocarbon conversion reactions in the steam catalytic cracking reactor.

In some embodiments, the steam catalytic cracking reactor comprises three separate beds, at least two of which comprise silicon carbide granules. In other embodiments, steam makes up between about 10 wt. % and about 50 wt. % of a mixed flow of hydrocarbons and steam to the steam catalytic cracking reactor. Still in other embodiments, the hydrocarbon inlet comprises a mixed paraffin flow, and the steam catalytic cracking reactor operates at a temperature at between about 300° C. to about 400° C. In some embodiments, the mixed paraffin flow comprises at least one compound selected from the group consisting of: $C_{10}H_{22}$, $C_{11}H_{24}$, $C_{12}H_{26}$, $C_{13}H_{28}$, and $C_{14}H_{30}$. Still in other embodiments, the products produced from hydrocarbon conversion reactions in the steam catalytic cracking reactor include at least one compound selected from the group consisting of: benzene, toluene, xylenes, and methyl(s), ethyl(s), and propyl(s) benzene products. In certain embodiments, the product separation unit separates hydrocarbon products by cooling.

In certain embodiments, the steam catalytic cracking reactor selectively converts a mixed paraffin feed to alkylbenzene compounds with at least about 30% selectivity for at least about 20 hours. Still in other embodiments, the steam catalytic cracking reactor conversion rate of a mixed paraffin feed is at least about 90% for at least about 20 hours. Still in other embodiments, the hydrocarbon inlet comprises a mixed paraffin flow comprising at least one compound selected from the group consisting of: octane, nonane, decane, undecane, dodecane, tridecane, and tetradecane. In some embodiments, the hydrocarbon inlet comprises a mixed isoparaffin flow comprising at least one compound selected from the group consisting of: an isomer of octane, an isomer of nonane, an isomer of decane, an isomer of undecane, an isomer of dodecane, an isomer of tridecane, and an isomer of tetradecane.

In some embodiments, the hydrocarbon inlet comprises a mixed olefin flow comprising at least one compound selected from the group consisting of: an olefin of octane, an olefin of nonane, an olefin of decane, an olefin of undecane, an olefin of dodecane, an olefin of tridecane, and an olefin of tetradecane. Still in other embodiments, the steam catalytic cracking reactor is operable to regenerate the externally-pore-blocked, internally-pore-opened modified zeolite crystals of the various methods and systems under air and increased temperature.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

So that the manner in which the features and advantages of the embodiments of systems and methods for continuously producing consistently-sized and characterizable externally-pore-blocked, internally-pore-opened modified zeolite crystals, as well as others, which will become apparent, may be understood in more detail, a more particular description of the embodiments of the present disclosure briefly summarized previously may be had by reference to the embodiments thereof, which are illustrated in the appended drawings, which form a part of this specification. It is to be noted, however, that the drawings illustrate only various embodiments of the disclosure and are therefore not to be considered limiting of the present disclosure's scope, as it may include other effective embodiments as well.

Figure 1:
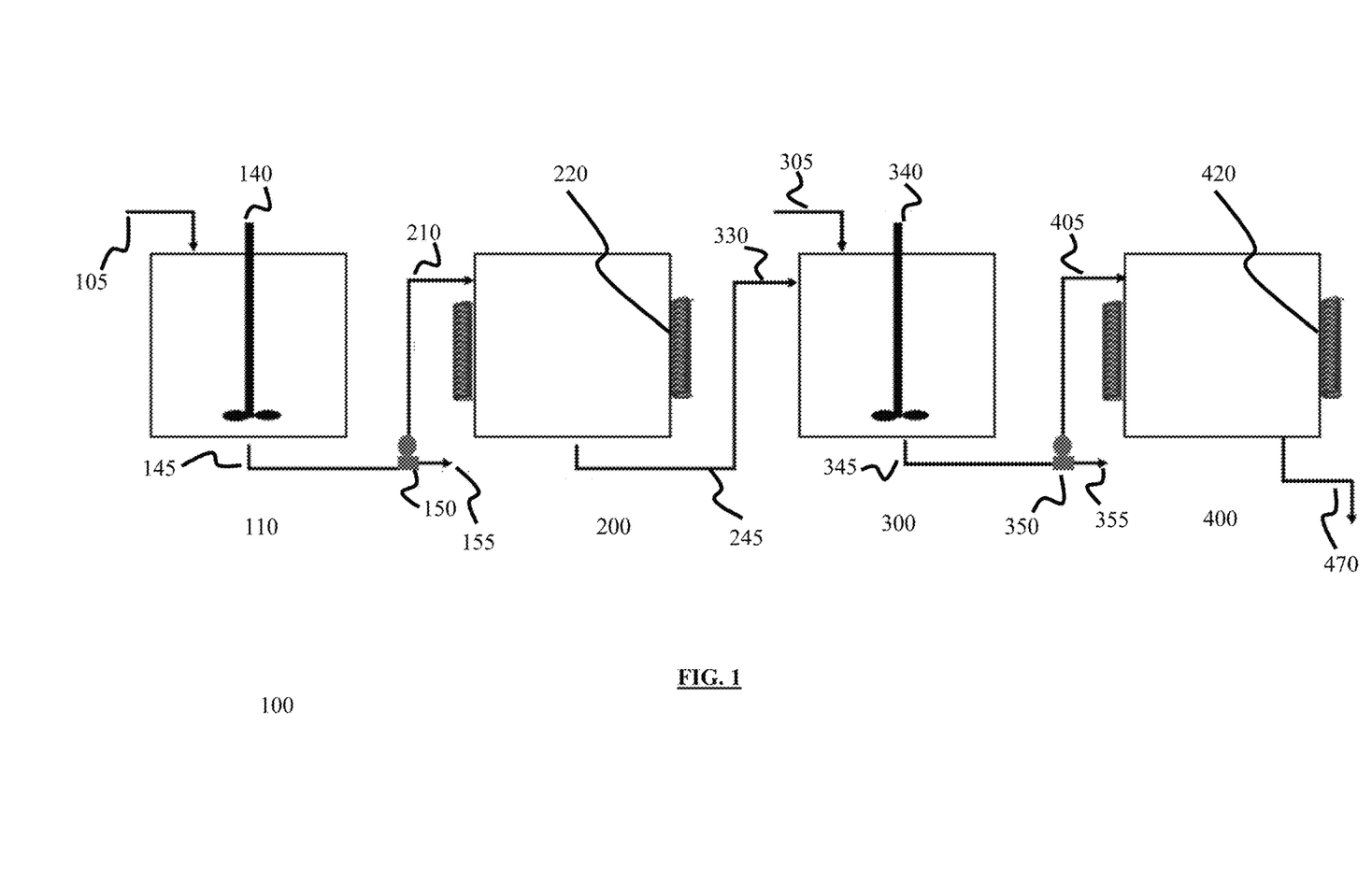
FIG. 1 is a schematic diagram showing an example system and process for blocking external pores and opening internal pores of zeolite material via deposition of silica over external pores and placement, followed by subsequent removal, of at least one organic blocking agent on internal pores.

Referring first to FIG. 1, a schematic diagram is provided showing an example system and process for blocking external pores and opening internal pores of zeolite material via deposition of silica over external pores and placement, followed by subsequent removal, of at least one organic blocking agent on internal pores. In external pore blocking system 100, four units are fluidly coupled and can be run in system or batch processes, the units including first stage internal pore blocker unit 110, second stage internal pore blocker unit 200, external pore blocker unit 300, and calcination unit 400.

Referring to an example embodiment for the use of system 100, a zeolite catalyst of ZSM-5-type structure with a silica to alumina molar ratio of between about 20 to about 500 is selected and introduced to first stage internal pore blocker unit 110 via line 105. The molar ratio is selected based in part on the required conversion and product selectivity for converting hydrocarbons. A low molar ratio of Si:Al means higher acidity of the catalyst, while the higher the ratio the lower the acidity. In one embodiment, the zeolite input into first stage internal pore blocker unit 110 via line 105 is in protonated form with hydrogen from hydrogenation or with ammonia from reaction with an ammonium-containing compound. In one embodiment, about 12 kg of zeolite is input into first stage internal pore blocker unit 110 via line 105 in a protonated form, but the systems and processes discussed here can be scaled for industrial application.

Next, a mixture of about 1 kg of organic pore blocking agent is pre-mixed with about 68 kg of water and is introduced via line 105 to first stage internal pore blocker unit 110, and stirring of the unit is carried out via stirring rod 140 at a speed of about 200 to about 300 rpm for about 2 to about 3 hours. First stage internal pore blocker unit 110 operates at a temperature between about 15° C. to about 40° C., and continuous heating need not be applied to the unit. The organic pore blocking agent enters mostly only the internal pores of the zeolite material. In some embodiments, internal pore blocking agent does not block external pores, and/or does not block external pores from being later-blocked by a silica agent during calcining.

Without being bound by any theory or practice, the pore blocking organic agents include long straight-chain hydrocarbon molecules that enter internal zeolite pores. After removal of the solvent (water), the internal pores will be occupied by the long straight-chain hydrocarbons. However, at the external pores, the long straight-chain hydrocarbon molecules are unlikely to be disposed because the external pores are too small or "short" to uptake the long straight-chain hydrocarbon molecules.

After mixing in first stage internal pore blocker unit 110, the zeolite solution is evacuated via line 145 to inline centrifuge unit 150 to separate a light phase from a heavy phase, the heavy phase including the zeolite powder with organic pore blocking agent incorporated into the internal pores. The light phase includes aqueous solution and is removed from the process via line 155, and the zeolite material of ZSM-5 is evacuated via line 210 to second stage internal pore blocker unit 200.

In second stage internal pore blocker unit 200, the unit operates to further block internal pores once the zeolite is received via line 210. The unit operates two different isothermal stages under static atmospheric air, in some embodiments. The first isothermal stage includes heating the zeolite via heating element 220 to between about 105° C. and about 115° C., preferably about 110° C. for between about 12 and about 18 hours, in order to dry the zeolite from moisture and remaining water. The second isothermal stage includes heating the zeolite via heating element 220 to between about 250° C. and about 350° C., preferably about 300° C., at a ramp rate of between about 2-3° C./min, and then maintaining the temperature for between about 12 and about 18 hours, in order to have the internal pores of zeolite of ZSM-5-type structure blocked by partially decomposing the organic pore blocking agent inside the internal pores.

The temperature in second stage internal pore blocker unit 200 is finally cooled down to between about 15° C. and about 40° C., and the zeolite material with internal pore blocking is evacuated via line 245 and proceeds to inlet 330 to enter external pore blocker unit 300.

In external pore blocker unit 300, blocking of the external pores of the zeolite is effected without further pore blocking of the internal pores. In one embodiment for the use of external pore blocker unit 300, an external-pore-blocking silica agent includes a mixture of orthosilicate compound, such as about 2 kg of tetrabutyl orthosilicate, mixed in about 50 kg of organic solvent of isopropanol. The tetrabutyl orthosilicate and organic solvent can be pre-mixed and then added to external pore blocker unit 300 via line 305.

Next, in external pore blocker unit 300, the zeolite material, silica agent and organic solvent are mixed via stirring rod 340 for between about 1 to about 2 hours at a speed between about 200 and about 300 rpm. In some embodiments, the unit does not require heating, and the mixture of solution would be in the range of temperature from about 15° C. to about 40° C. Afterward, the zeolite material and silica agent are evacuated via line 345 to inline centrifuge unit 350 to separate the heavy zeolite material from a light phase, which includes remaining silica agent mixed with organic solvent liquid. The light phase is removed via line 355. Next, the zeolite material is evacuated and sent to calcination unit 400 via line 405.

In calcination unit 400, dual functions are carried out, both opening of the internal pores of the zeolite material by application of high temperature, which causes removal of the organic pore blocking agent from internal pores via de-coking in addition to or alternative to cracking, and semi-permanent to permanent blocking of the external pores by formation of at least one silicon oxide (silica) layer from silica of the silica agent. In some embodiments, the unit operates by applying two isothermal steps under static atmospheric air. The first isothermal stage is applied by heating calcination unit 400 via heating element 420 to between about 105° C. and about 115° C., preferably about 110° C. for between about 12 to about 18 hours to dry the zeolite from any remaining isopropanol organic solvent, or any other suitable organic solvent. The second isotherm stage is applied by heating calcination unit 400 via heating element 420 to between about 585° C. and about 615° C., preferably about 600° C., at a ramp rate of about 2-3° C./min, and then maintaining the temperature for between about 12 hours and about 18 hours. This allows the modified ZSM-5 zeolite catalyst to have open internal pores by completing the decomposition of the organic pore blocking agent from internal pores of the zeolite.

In addition, the external pores of the zeolite are blocked by silicon oxide (silica) after completing conversion of the orthosilicate compound into silica over the external pores of the zeolite. The final modified externally-pore-blocked, internally-pore-opened zeolite catalyst product, for example modified ZSM-5 catalyst product, is evacuated via line 470 for use as a catalyst, optionally in steam catalytic cracking, at the end of the process once it is cooled down to between about 15° C. and about 40° C. The zeolite material of ZSM-5 product is now active and the material can be saved in a closed container away from moisture for catalysis reactions.

The modified zeolite catalyst product produced by the system and process of FIG. 1 is surprisingly and unexpectedly well suited as a catalyst under steam catalytic cracking conditions. In some embodiments, the modified zeolite catalyst is sent to an extruder to add about 50-60 wt. % of alumina binder before use in a reaction for hydrocarbon conversions under steam, either low or high concentration steam. Adding alumina binder aims to reduce the cost of zeolite and increase the mechanical strength of zeolite catalyst, along with heat resistance and stability. The extrusion binder in some embodiments does not have any effect on the zeolite conversion/selectivity performance or pore blocking. In one embodiment, not pictured in FIG. 1, after calcination unit 400, modified ZSM-5 is sent to a catalyst extrusion unit to add alumina binder in the range of 50-60 wt. %, followed by drying for 24 hours at room temperature, followed by drying at 100° C. for 24 hours, and followed by calcination again at 550° C. Afterwards, a zeolite with 50-60 wt. % binder is prepared to be used as a reaction catalyst, for example in hydrocracking reactions.

Figure 2:
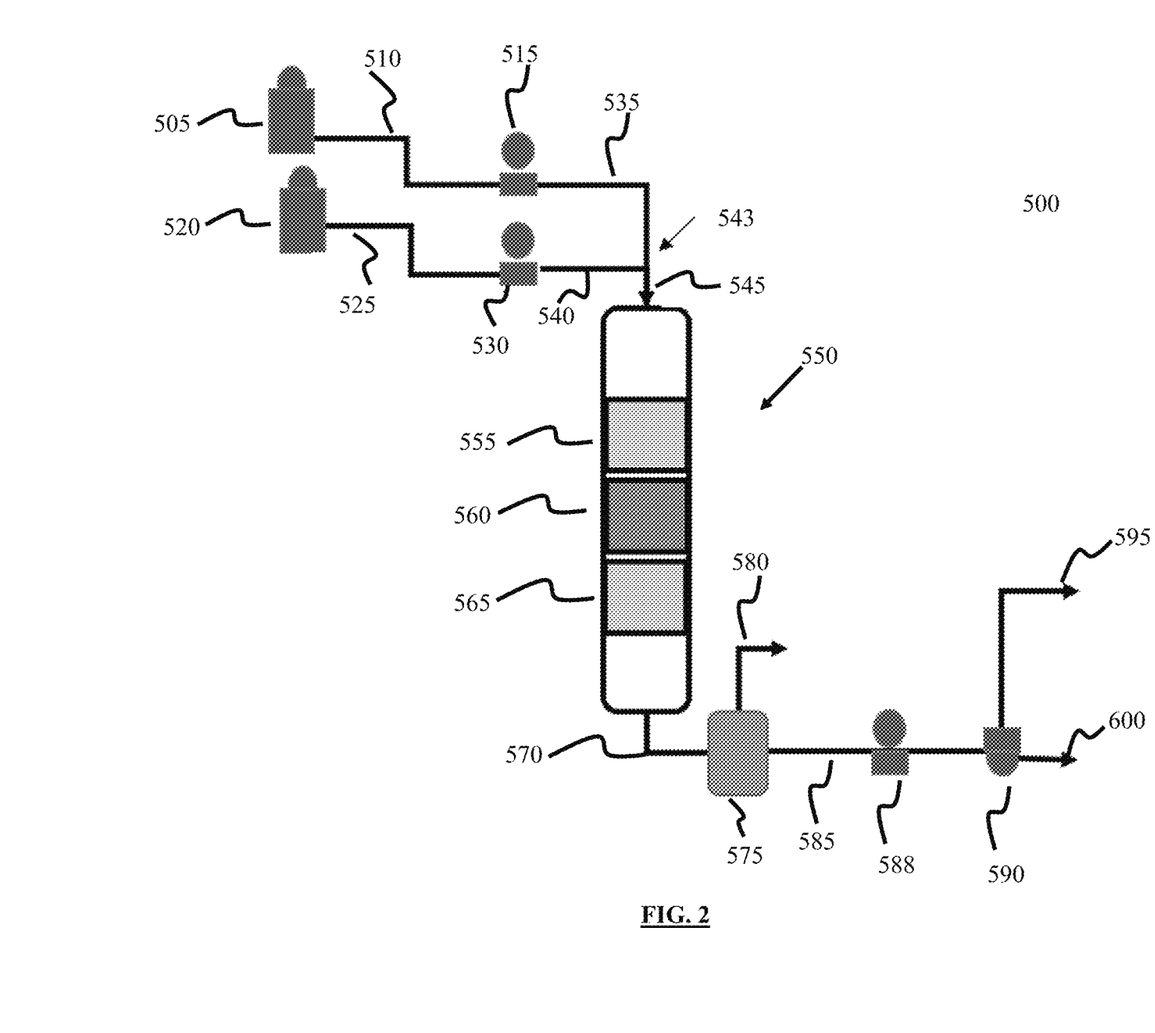
FIG. 2 is a schematic diagram showing an example catalytic fixed bed system for steam catalytic conversion of paraffin, iso-paraffin, and olefin feedstocks to alkylbenzenes using modified catalysts of the present disclosure.

Referring now to FIG. 2, a schematic diagram is provided showing an example catalytic fixed bed system for steam catalytic conversion of paraffin, iso-paraffin, and olefin feedstocks to alkylbenzenes. Modified zeolite catalysts produced by the system and process of FIG. 1 can be used in the system of FIG. 2. Reactor system 500 includes a single fixed bed reactor 550, but in other embodiments more reactors could be used in series or parallel, and other suitable types of reactors could be used with modified zeolite catalysts, such as up-flow and down-flow reactors.

Reactor system 500 includes water tank 505 to produce steam in reactor 550 and hydrocarbon supply tank 520 to supply hydrocarbons to reactor 550. Pumps 515, 530 control water flow in line 510 and hydrocarbon flow in line 525, respectively. Steam supplied to reactor 550 can make up between about 10 wt. % to about 50 wt. % of the total steam plus hydrocarbon flow to reactor 550. Liquid hour space velocity (LHSV) requirements for steam in reactor 550 are between about 0.5 $h^{-1}$ and about 20 $h^{-1}$ at standard temperature and pressure (STP), in some embodiments.

The hydrocarbon feed stream can include at least about 50 wt. % to about 90 wt. % of paraffins, iso-paraffins, or/and olefins. LHSV requirements for hydrocarbon feed in reactor 550 are between about 0.5 $h^{-1}$ and about 20 $h^{-1}$ at standard temperature and pressure (STP), in some embodiments. Pumps 515, 530 deliver liquid water and hydrocarbons via pre-heated lines 535, 540, respectively, to a tee connection 543 where the water and hydrocarbon feeds are mixed. The lines 535, 540 are heated from between about 10° C. to about 250° C., and preferably between about 150° C. to about 200° C. The mixed hydrocarbon and water (steam) feed enters reactor 550 via line 545.

In the embodiment shown, reactor 550 includes three fixed bed zones: first bed zone 555; second bed zone 560; and third bed zone 565. In this way, reactor 550 is configured as a steam catalytic reactor unit. In the embodiment shown, reactor 550 is a fixed bed reactor type, and the mixed hydrocarbon and water feed is introduced from the top via line 545 and proceeds downwardly through reactor 550 by gravity. In one embodiment, reactor 550 operates at static atmospheric pressure, and no air is introduced to reactor 550 during hydrocarbon conversion reactions.

Reactor 550 is heated by one or more electrical heater or other source of heating (not pictured) in order to provide heating for the water and hydrocarbon reactants at between about 300° C. to about 400° C., preferably in the range of about 325° C. to about 375° C. In the embodiment shown, first bed zone 555 and third bed zone 565 mostly comprise granules of silicon carbide in a granule size range of about 1 mm to about 50 mm. Second bed zone 560 comprises modified zeolite material made in the system and process of FIG. 1, for example externally-pore-blocked, internally-pore-opened modified ZSM-5 zeolite catalyst in optional alumina binder. First bed zone 555, second bed zone 560, and third bed zone 565 are heated and temperatures are monitored and controlled in order to maintain proper heating of fluid streams from line 545.

In reactor 550, both the hydrocarbons and steam contact first bed zone 555 for proper heat transfer between the vapors of both feeds before contacting the second bed zone 560 for reaction and conversion of hydrocarbons, including paraffins, iso-paraffins and/or olefins, via zeolite internal pore catalysis. The reactions in second bed zone 560, catalyzed by the improved and modified externally-pore-blocked, internally-pore-opened zeolite catalyst, produce alkylbenzenes and other byproducts and isomers, such as naphthene, olefins, and smaller molecules of paraffins.

After reacting in second bed zone 560 and proceeding through third bed zone 565, the products and byproducts exit reactor 550 via line 570 and proceed to cooling gas-liquid separator 575. Cooling is applied in cooling gas-liquid separator 575 to reach a temperature between about 3° C. to about 25° C., preferably between about 5° C. and about 10° C. A gas composition is sent out of cooling gas-liquid separator 575 via line 580. This gas composition is about 0.1 wt. % to about 25 wt. % of the total product in cooling gas-liquid separator 575 and comprises mainly hydrogen, methane, ethane, ethylene, propane, propylene, butane, isobutane, and butenes.

Liquid products from cooling gas-liquid separator 575 are sent to inline liquid pump 588 via line 585 to pump a liquid phase of water and hydrocarbon to inline centrifuge 590. In the embodiment shown, inline centrifuge 590 does not require any demulsifier chemicals, and it operates at temperature from about 5° C. to about 75° C., preferably between about 15° C. and about 35° C. Inline centrifuge 590 separates a light phase of hydrocarbon from a heavy aqueous phase. The light phase is sent to a product tank (not shown) via line 595. The heavy aqueous phase including water is sent out via line 600. Water is optionally recycled to reactor 550 (not shown). By processing zeolite material of ZSM-5 via four modification steps shown in FIG. 1, the zeolite is made stable for use as a catalyst under steam, and the reactivity and conversion of hydrocarbons increases under low and high concentration steam streams for on-purpose conversion of paraffins, iso-paraffins, and/or olefins (from carbon number 6 to carbon number 14) to alkylbenzenes via a steam fixed bed reactor, such as reactor 550.

The hydrocarbon product separated from the aqueous phase is about 30 wt. % to about 60 wt. % of the total products in inline centrifuge 590, and it includes aromatics, mainly alkyl benzenes of benzene, such as toluene, xylenes, and methyl(s), ethyl(s), and propyl(s) benzene products. In some embodiments, the system and process of FIG. 2 applying the modified externally-pore-blocked, internally-pore-opened zeolite catalyst product of FIG. 1 achieved a high level of conversion of paraffins in the range of 90% to 100% conversion (see Examples 1 and 2 described as follows). The byproducts comprise mainly reformate product, which can be sent to a gasoline pool to upsurge octane numbers by producing iso-paraffins, naphthalenes, and olefins.

Figure 3:
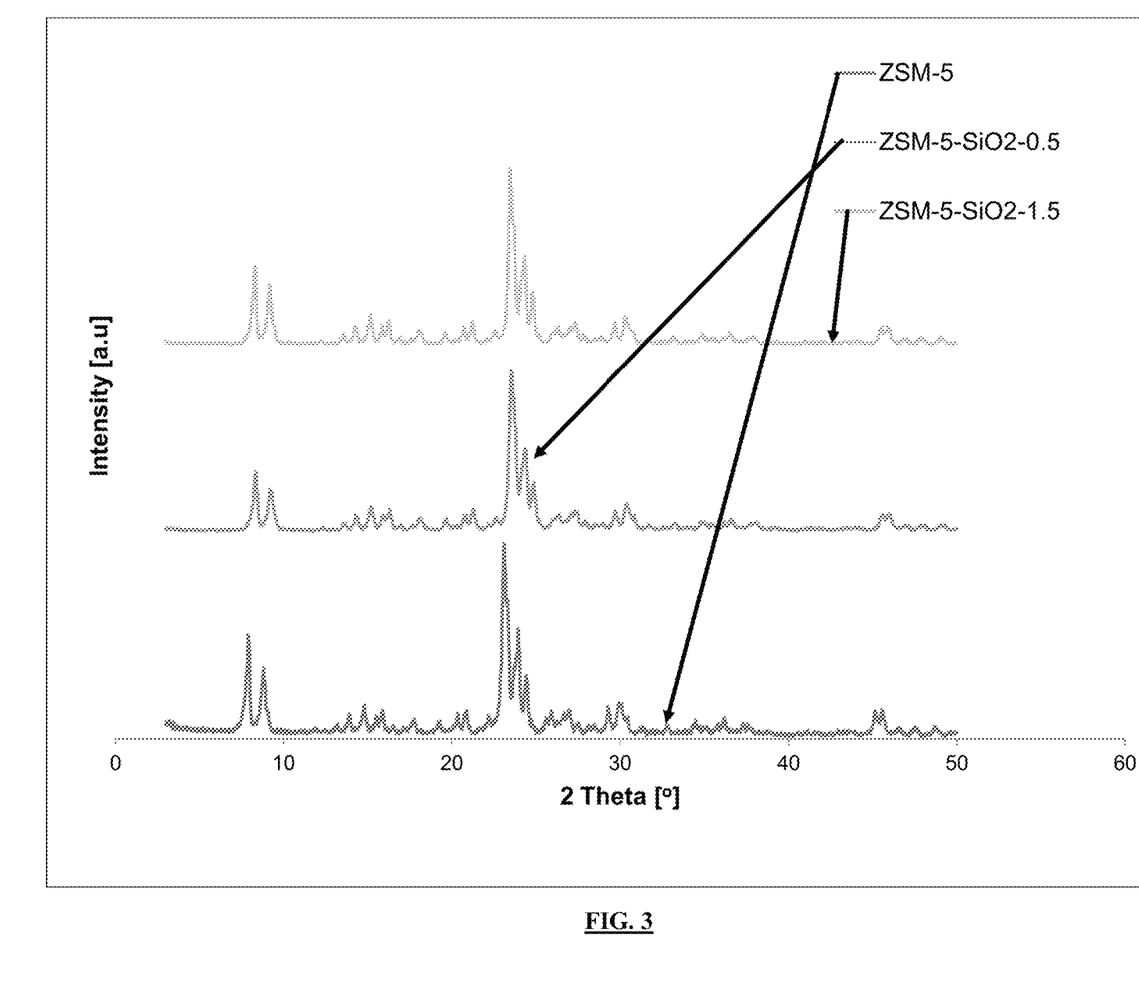
FIG. 3 shows X-ray diffraction (XRD) patterns of original ZSM-5 zeolite and two externally-pore-blocked, internally-pore-opened modified ZSM-5 zeolites, where the external pores were blocked by silica.

Referring now to FIG. 3, X-ray diffraction (XRD) patterns are shown of original ZSM-5 zeolite and two externally-pore-blocked, internally-pore-opened modified ZSM-5 zeolites, where the external pores were blocked by silica. External pores in two separate embodiments were blocked by 0.5 wt. % and 1.5 wt. % silica from the applied orthosilicate compound. The XRD confirms the structure of the ZSM-5 framework is maintained, and no negative effect on the framework of the structure occurs after the modification steps of FIG. 1.

Example 1: Steam Catalytic Cracking Applying Internally-Pore-Opened, Externally-Pore Blocked Modified Zeolite Catalyst at 10 Vol. % Steam Steam catalytic cracking was effected using a feed stream comprising 10% by volume water (for steam) mixed with 90% by volume of paraffin feedstock comprising $C_{10}H_{22}$, $C_{12}H_{26}$, $C_{13}H_{28}$, and $C_{14}H_{30}$. Catalytic conversion of the hydrocarbons was carried out in order to produce aromatics such as alkylbenzenes. Both feedstocks were pre-heated at 150° C. before entering into a reactor, for example the reactor shown in FIG. 2. LHSV of about 4 $h^{-1}$ and a reaction temperature of about 350° C. were used. A zeolite of ZSM-5 was selected with a silica to alumina molar ratio of 50, and then the zeolite was modified by first blocking the internal pores of the zeolite with an organic pore blocking agent. External pores of the zeolite were blocked by a silica layer of 0.5 wt. % of total zeolite weight, and this was followed by opening the internal pores by calcining the zeolite to decompose the organic pore blocking agent away from the internal pores. Results of Example 1 are shown in Table 1.

TABLE 1

Results from Example 1 for steam catalytic cracking of paraffin feedstock to produce alkylbenzene products and reformate byproducts with 10 vol. % of steam.

| Time of Stream | Conversion, Vol. % | Alkylbenzene Selectivity, Vol. % | Isoparaffins and Naphthenes Selectivity, Vol. % |
| --- | --- | --- | --- |
| 2 hours | 100% | 57% | 24% |
| 4 hours | 100% | 60% | 22% |
| 18 hours | 97% | 52% | 24% |
| 20 hours | 98% | 49% | 27% |

Example 2: Steam Catalytic Cracking Applying Internally-Pore-Opened, Externally-Pore Blocked Modified Zeolite Catalyst at 20 Vol. % Water (for Steam)

The modified ZSM-5 zeolite catalyst of Example 1 was regenerated via air exposure, and the air gas hourly space velocity was set at 100 $h^{-1}$ at 550° C. for 5 hours. Afterward, the reactor temperature was reduced to 350° C., and nitrogen gas was introduced at a gas hourly space velocity of 100 $h^{-1}$ to remove air from the reactor. Then a mixed water and hydrocarbon stream comprising 80 vol. % paraffin feedstock and 20 vol. % water (for steam) was sent to the reactor at a LHSV of 4 $h^{-1}$. The conversion and selectivity results of Example 2 are shown in Table 2.

TABLE 2

Results from Example 2 for steam catalytic cracking of paraffin feedstock to produce alkylbenzene products and reformate byproducts with 20 vol. % of water (for steam).

| Time of Stream | Conversion, Vol. % | Alkylbenzene Selectivity, Vol. % | Isoparaffins and Naphthenes, Selectivity, Vol. % |
| --- | --- | --- | --- |
| 2 hours | 98% | 45% | 27% |
| 4 hours | 95% | 46% | 24% |
| 5 hours | 98% | 51% | 24% |

In some embodiments disclosed here, the organic pore blocking agent comprising one or more organic pore blocking compounds is applied in a range of between about 2 wt. % to about 15 wt. % of the total zeolite material weight, preferably applied in a range of between about 5 wt. % to about 10 wt. % of the total zeolite material weight. In some embodiments, a unit to apply organic pore blocking agent to internal pores of a zeolite operates two isotherm stages under static atmospheric air. In a first isotherm stage, the zeolite material is heated to dry the zeolite of moisture at between about 105° C. to about 115° C., preferably about 110° C., for between about 12 hours to about 18 hours. In a second isotherm stage, the zeolite material is heated to between about 250° C. and about 300° C. at a ramp rate of about 2-3° C./min, and the temperature is maintained for between about 12 and about 18 hours in order to further block the internal pores via coking and decomposition of the organic pore blocking material.

Organic blocking agents include one or more of hexadecane ($C_{16}H_{34}$), heptadecane ($C_{17}H_{36}$), octadecane ($C_{18}H_{38}$), nonadecane ($C_{19}H_{40}$), icosane ($C_{20}H_{42}$), heneicosane ($C_{21}H_{44}$), cetyltrimethylammonium, cetyltrimethylammonium bromide, behentrimonium chloride, or 1-bromohexadecane.

In some embodiments disclosed here, external pore blocking agents can include one or more orthosilicate compounds such as tetraethyl orthosilicate, tetrabutyl orthosilicate, dichlorodimethylsilane, silicon 2-ethylhexanoate, or tetrahexyl orthosilicate. Organic solvent of the external pore blocking agent to dissolve one or more orthosilicates can include one or more of methanol, ethanol, 1-propanol, 2-propanol, n-butanol, sec-butanol, and isobutanol. In some embodiments, an external pore blocking agent is made from one or more orthosilicate compounds dissolved in one or more organic solvents, and the external pore blocking agent is used to coat external pores of a zeolite material with a silica layer. In some embodiments, a calcination stage conducted at two separate isothermal temperatures allows for both internal pore re-opening via decomposition of the organic pore blocking agent and external pore blocking via silicon dioxide deposition and hardening. In some embodiments, a calcination unit operates two isotherm stages and performs dual functions to open internal pores at high temperature by cracking the pore blocking organic agent and blocking the external pores by forming a silicon oxide (silica) layer from the external pore blocking agent comprising orthosilicate and an organic solvent.

The deposited silica layer after calcining can be between about 0.1 wt. % to about 10 wt. % of the total modified zeolite weight. Preferably, the deposited silica layer after calcining is between about 0.3 wt. % to about 5 wt. % of the total modified zeolite weight. Calcining temperature to open internal pores by removing organic pore blocking agent can be between about 500° C. and about 750° C., preferably between about 550° C. and about 650° C. under static air, or under a mixture of about 5 vol. % to about 20 vol. % oxygen gas in nitrogen, or under a mixture of about 5 vol. % to about 20 vol. % oxygen gas in helium, or under a mixture of about 5 vol. % to about 20 vol. % oxygen gas in argon gas.

Steam catalytic cracking/conversion of hydrocarbons can be carried out over the modified zeolites using about 10 wt. % to about 50 wt. % steam for on-purpose conversion of paraffins, isoparaffins, and/or olefins to alkylbenzenes. Steam/water and make-up hydrocarbon feed streams can be initially heated prior to entering a catalytic reactor to a temperature at between about 40° C. to 250° C., preferably between about 120° C. to about 200° C. A steam catalytic reactor suitable for hydrocarbon conversion reactions described herein can be operated at a temperature between about 300° C. to about 400° C., preferably in the range of about 325° C. to about 375° C. A suitable LHSV range in reactors of the present disclosure includes between about between about 0.5 h$^{-1}$ to about 20 h$^{-1}$ at STP.

Light phase liquid products produced from steam catalytic cracking over modified zeolite catalysts of the present disclosure and separated from heavy byproducts, for example by cooling separation and inline centrifuge, contain benzene, toluene, xylenes, and methyl(s), ethyl(s), and propyl(s) benzene products at least at between about 20 wt. % to about 50 wt. % of the total light liquid phase products. Byproducts produced along with light phase liquid products include isoparaffins, naphthalenes, and olefins at about 10 wt. % to about 40 wt. % of the total light liquid phase products, and these can be sent for mixing to a gasoline pool. In some embodiments of systems and methods disclosed here, demulsifiers are not required for use with inline centrifuges.

Suitable hydrocarbon feedstocks for steam catalytic cracking over modified zeolite catalysts of the present disclosure include one or more of octane, nonane, decane, undecane, dodecane, tridecane, and tetradecane. Suitable isoparaffin feedstocks can include one or more of an isomer of octane, an isomer of nonane, an isomer of decane, an isomer of undecane, an isomer of dodecane, an isomer of tridecane, and an isomer of tetradecane. Suitable olefin feedstocks can include one or more of an olefin of octane, an olefin of nonane, an olefin of decane, an olefin of undecane, an olefin of dodecane, an olefin of tridecane, and an olefin of tetradecane. Suitable hydrocarbon feedstocks for treatment can arise from a distillation unit, a fluidized catalytic cracking unit, a reformer unit, a dealkylation unit, an isomerization unit, or a cracker unit. Organic sulfur impurities of acceptable feedstocks can range from about 1 ppm to about 10,000 ppm.

The term "about" when used with respect to a value or range refers to values including plus and minus 5% of the given value or range.

The singular forms "a," "an," and "the" include plural referents, unless the context clearly dictates otherwise.

In the drawings and specification, there have been disclosed embodiments of systems and methods for continuously producing consistently-sized and characterizable externally-pore-blocked, internally-pore-opened modified zeolite crystals, and although specific terms are employed, the terms are used in a descriptive sense only and not for purposes of limitation. The embodiments of the present disclosure have been described in considerable detail with specific reference to these illustrated embodiments. It will be apparent, however, that various modifications and changes can be made within the spirit and scope of the disclosure as described in the foregoing specification, and such modifications and changes are to be considered equivalents and part of this disclosure.

What is claimed is:

1. A method for production of externally-pore-blocked, internally-pore-opened modified zeolite crystals, the method comprising the steps of:
   mixing zeolite crystals with an organic pore blocking agent;
   heating the zeolite crystals mixed with the organic pore blocking agent to dry the zeolite crystals and block internal pores of the dried zeolite crystals and produce internally-pore-blocked zeolite crystals via decomposition of the organic pore blocking agent;
   mixing the internally-pore-blocked zeolite crystals with an external pore blocking agent to coat external pores; and
   calcining the internally-pore-blocked zeolite crystals mixed with the external pore blocking agent, to re-open internal pores via decomposition of the organic pore blocking agent and to block external pores via formation of a silica layer over external pores of the zeolite crystals, forming the externally-pore-blocked, internally-pore-opened modified zeolite crystals.

2. The method according to claim 1, where the zeolite crystals comprise ZSM-5 zeolite crystals.

3. The method according to claim 1, where the zeolite crystals comprise at least one zeolite selected from the group consisting of: faujasite, Beta zeolite, Mordenite zeolite, ZSM-5, ZSM-11, Ferrierite, MCM-22, SBA-15, ZSM-12, EU-1, ZSM-22, ZSM-23, ZSM-35, ZSM-39, SSZ-13, SSZ-24, SAPO-18, SAPO-34, SAPO-37, SAPO-41, SAPO-44, Sililcalite-1, AlPO4, AlPO-11, AlPO-16, AlPO-18, Linde zeolite of LTA, LTL, OOF, or MER, CIT-5, UTD-1, and Erionite.

4. The method according to claim 1, where the organic pore blocking agent is mixed with the zeolite crystals at a weight between about 2 wt. % to about 15 wt. % of the weight of the zeolite crystals.

5. The method according to claim 1, where the organic pore blocking agent is mixed with the zeolite crystals at a weight between about 5 wt. % to about 10 wt. % of the weight of the zeolite crystals.

6. The method according to claim 1, where the zeolite crystals are in a protonated form.

7. The method according to claim 1, where the step of mixing zeolite crystals with an organic pore blocking agent includes mixing in an aqueous solution for between about 2 and about 3 hours without heating.

8. The method according to claim 1, where the step of heating the zeolite crystals mixed with the organic pore blocking agent comprises a first step of heating the zeolite crystals mixed with the organic pore blocking agent to between about 105° C. and about 115° C. for between about 12 and about 18 hours, in order to dry the zeolite crystals from moisture.

9. The method according to claim 8, where the step of heating the zeolite crystals mixed with the organic pore blocking agent comprises a second step of heating the zeolite crystals mixed with the organic pore blocking agent to between about 250° C. and about 350° C. for between about 12 and about 18 hours, in order to have internal pores of the zeolite crystals blocked by partially decomposing the organic pore blocking agent inside internal pores.

10. The method according to claim 1, where the organic pore blocking agent includes at least one compound selected from the group consisting of: hexadecane, heptadecane, octadecane, nonadecane, icosane, heneicosane, cetyltrimethylammonium, cetyltrimethylammonium bromide, behentrimonium chloride, and 1-bromohexadecane.

11. The method according to claim 1, where the step of mixing the internally-pore-blocked zeolite crystals with an external pore blocking agent comprises mixing the external pore blocking agent comprising an orthosilicate compound and an organic solvent.

12. The method according to claim 11, where the orthosilicate compound comprises at least one compound selected from the group consisting of: tetraethyl orthosilicate, tetrabutyl orthosilicate, dichlorodimethylsilane, silicon 2-ethylhexanoate, and tetrahexyl orthosilicate.

13. The method according to claim 11, where the organic solvent comprises a compound selected from the group consisting of: methanol, ethanol, 1-propanol, 2-propanol, n-butanol, sec-butanol, and isobutanol.

14. The method according to claim 1, where the step of mixing the internally-pore-blocked zeolite crystals with an external pore blocking agent proceeds for between about 1 to about 2 hours without heating.

15. The method according to claim 1, where the step of calcining the internally-pore-blocked zeolite crystals mixed with the external pore blocking agent comprises a first step of heating to between about 105° C. and about 115° C. for between about 12 to about 18 hours to dry the zeolite from any organic solvent.

16. The method according to claim 15, where the step of calcining the internally-pore-blocked zeolite crystals mixed with the external pore blocking agent comprises a second step of heating to between about 500° C. and about 750° C. for between about 12 hours and about 18 hours.

17. The method according to claim 1, further comprising the step of extruding the externally-pore-blocked, internally-pore-opened modified zeolite crystals to add an alumina binder.

18. The method according to claim 1, where the externally-pore-blocked, internally-pore-opened modified zeolite crystals comprise a deposited external-pore-blocking silica layer at about 0.3 wt. % to about 5 wt. % of the total modified zeolite crystal weight.

19. The method according to claim 1, further comprising the step of using the externally-pore-blocked, internally-pore-opened modified zeolite crystals in steam catalytic cracking.

20. A steam catalytic cracking system to carry out hydrocarbon conversion reactions over the externally-pore-blocked, internally-pore-opened modified zeolite crystals of claim 1, the steam catalytic cracking system comprising:
a steam inlet;
a hydrocarbon inlet;
a steam catalytic cracking reactor comprising the externally-pore-blocked, internally-pore-opened modified zeolite crystals of claim 1 fluidly coupled to the steam inlet and the hydrocarbon inlet; and
a product separation unit fluidly coupled to the steam catalytic cracking reactor to separate products produced from hydrocarbon conversion reactions in the steam catalytic cracking reactor.

21. The system according to claim 20, where the steam catalytic cracking reactor comprises three separate beds, at least two of which comprise silicon carbide granules.

22. The system according to claim 20, where steam makes up between about 10 wt. % and about 50 wt. % of a mixed flow of hydrocarbons and steam to the steam catalytic cracking reactor.

23. The system according to claim 20, where the hydrocarbon inlet comprises a mixed paraffin flow, and the steam catalytic cracking reactor operates at a temperature at between about 300° C. to about 400° C.

24. The system according to claim 23, where the mixed paraffin flow comprises a compound selected from the group consisting of: $C_{10}H_{22}$, $C_{11}H_{24}$, $C_{12}H_{26}$, $C_{13}H_{28}$, and $C_{14}H_{30}$.

25. The system according to claim 20, where the products produced from hydrocarbon conversion reactions in the steam catalytic cracking reactor include at least one compound selected from the group consisting of: benzene, toluene, xylenes, and methyl, ethyl, and propyl benzene products.

26. The system according to claim 20, where the product separation unit separates hydrocarbon products by cooling.

27. The system according to claim 20, where the steam catalytic cracking reactor selectively converts a mixed paraffin feed to alkylbenzene compounds with at least about 30% selectivity for at least about 20 hours.

28. The system according to claim 20, where the steam catalytic cracking reactor conversion rate of a mixed paraffin feed is at least about 90% for at least about 20 hours.

29. The system according to claim 20, where the hydrocarbon inlet comprises a mixed paraffin flow comprising a compound selected from the group consisting of: octane, nonane, decane, undecane, dodecane, tridecane, and tetradecane.

30. The system according to claim 20, where the hydrocarbon inlet comprises a mixed isoparaffin flow comprising at least one compound selected from the group consisting of: an isomer of octane, an isomer of nonane, an isomer of decane, an isomer of undecane, an isomer of dodecane, an isomer of tridecane, and an isomer of tetradecane.

31. The system according to claim 20, where the hydrocarbon inlet comprises a mixed olefin flow comprising a compound selected from the group consisting of: an olefin of octane, an olefin of nonane, an olefin of decane, an olefin of undecane, an olefin of dodecane, an olefin of tridecane, and an olefin of tetradecane.

32. The system according to claim 20, where the steam catalytic cracking reactor is operable to regenerate the externally-pore-blocked, internally-pore-opened modified zeolite crystals of claim 1 under air.

* * * * *